(12) United States Patent  
Li

(10) Patent No.: US 9,095,406 B2
(45) Date of Patent: Aug. 4, 2015

(54) SHAPE MEMORY CONTROLLER

(75) Inventor: Jamie Li, Lexington, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 186 days.

(21) Appl. No.: 13/568,846

(22) Filed: Aug. 7, 2012

(65) Prior Publication Data

US 2013/0041207 A1 Feb. 14, 2013

Related U.S. Application Data

(60) Provisional application No. 61/521,225, filed on Aug. 8, 2011.

(51) Int. Cl.
*A61F 2/00* (2006.01)

(52) U.S. Cl.
CPC ....... *A61F 2/0036* (2013.01); *A61F 2210/0033* (2013.01); *A61F 2210/0042* (2013.01)

(58) Field of Classification Search
CPC ..... A61F 2/004; A61F 2/0004; A61F 2/0009; A61F 2/0013; A61F 2/0031; A61F 2/0036; A61F 2/0045; A61F 5/005; A61F 5/0056; A61F 5/0063
USPC ........ 600/29–31, 37; 606/151, 153, 155–157; 128/DIG. 25
See application file for complete search history.

(56) References Cited

U.S. PATENT DOCUMENTS

| | | | | |
|---|---|---|---|---|
| 4,556,050 | A | * | 12/1985 | Hodgson et al. ............... 600/30 |
| 4,634,443 | A | * | 1/1987 | Haber ............................ 600/31 |
| 4,878,889 | A | * | 11/1989 | Polyak ........................... 600/31 |
| 6,319,237 | B1 | | 11/2001 | Krumme |
| 2006/0074439 | A1 | * | 4/2006 | Garner et al. ................. 606/153 |
| 2007/0073098 | A1 | * | 3/2007 | Lenker et al. .................. 600/30 |
| 2010/0010518 | A1 | * | 1/2010 | Stopek et al. ................ 606/153 |

FOREIGN PATENT DOCUMENTS

| | | |
|---|---|---|
| EP | 0348114 B1 | 12/1991 |
| WO | 2013022956 A1 | 2/2013 |

OTHER PUBLICATIONS

International Preliminary Report on Patentability for International Application No. PCT/US2012/049974, mailed Feb. 20, 2014, 8 pages.

Search Report and Written Opinion for International Application No. PCT/US2012/049974, mailed Nov. 13, 2012, 13 pages.

* cited by examiner

*Primary Examiner* — Charles A Marmor, II

*Assistant Examiner* — Carrie R Dorna

(74) *Attorney, Agent, or Firm* — Brake Hughes Bellermann LLP

(57) ABSTRACT

An apparatus for selectively opening and closing a body lumen within a patient's body is provided. The apparatus includes an elongate member and a shape memory element. The elongate member is configured to at least partially surround the body lumen and defines a lumen. The shape memory element is disposed of adjacent to the lumen defined by the elongate member. Further, the shape memory element is adapted to change its configuration based on a change in temperature. These changes in the configuration of the shape memory element causes the apparatus to selectively move between a first configuration and a second configuration.

19 Claims, 12 Drawing Sheets

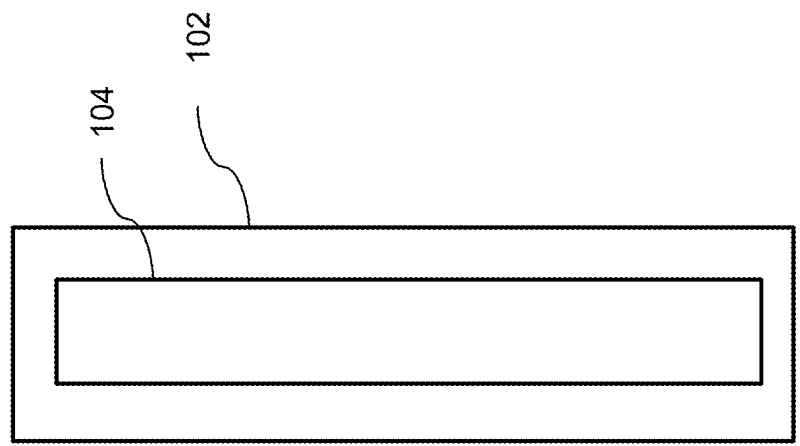

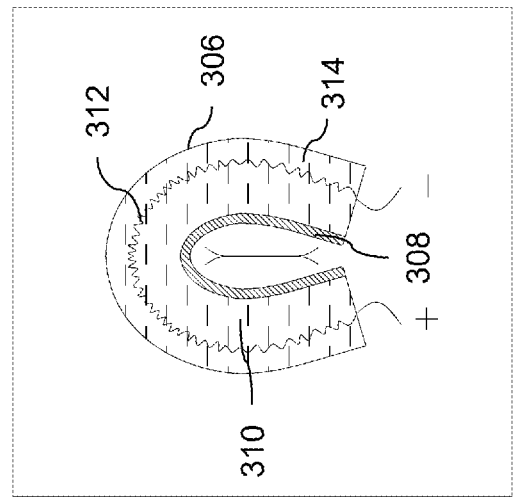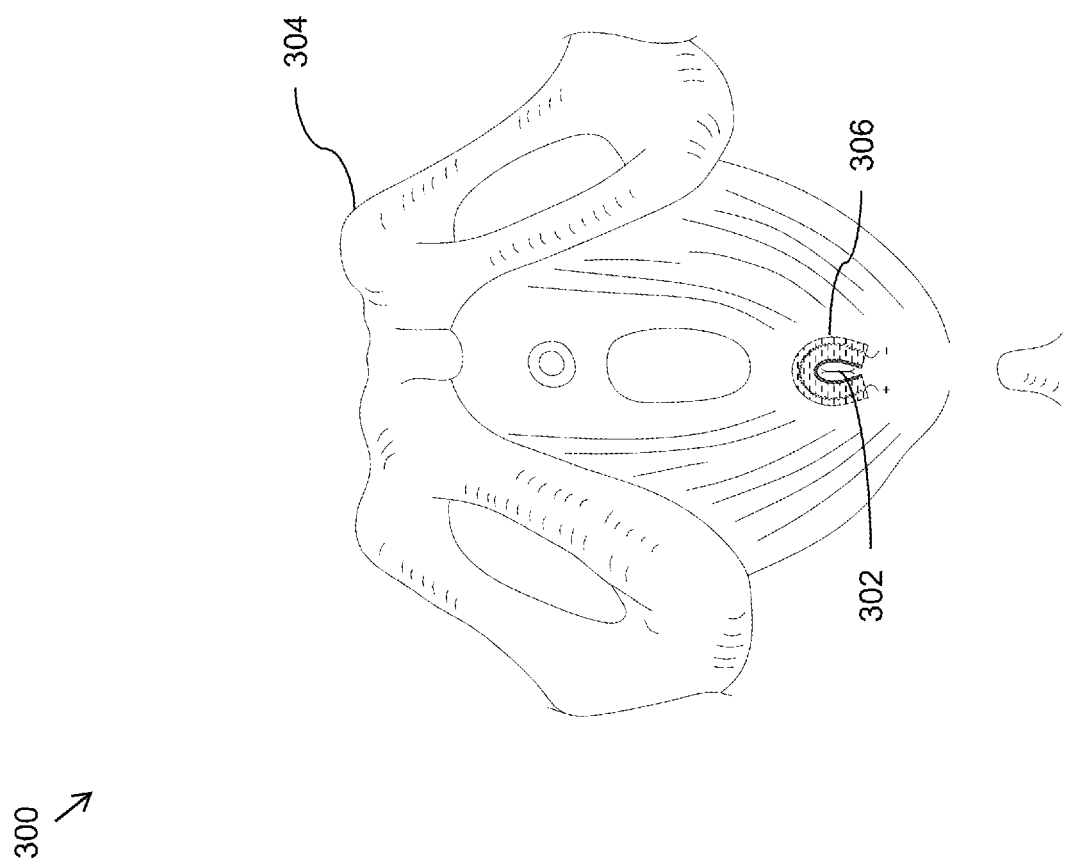
Fig. 3a

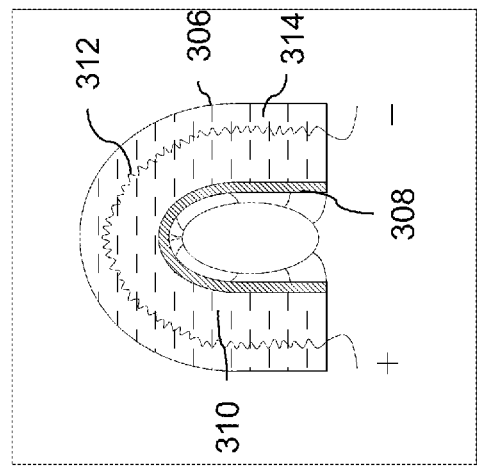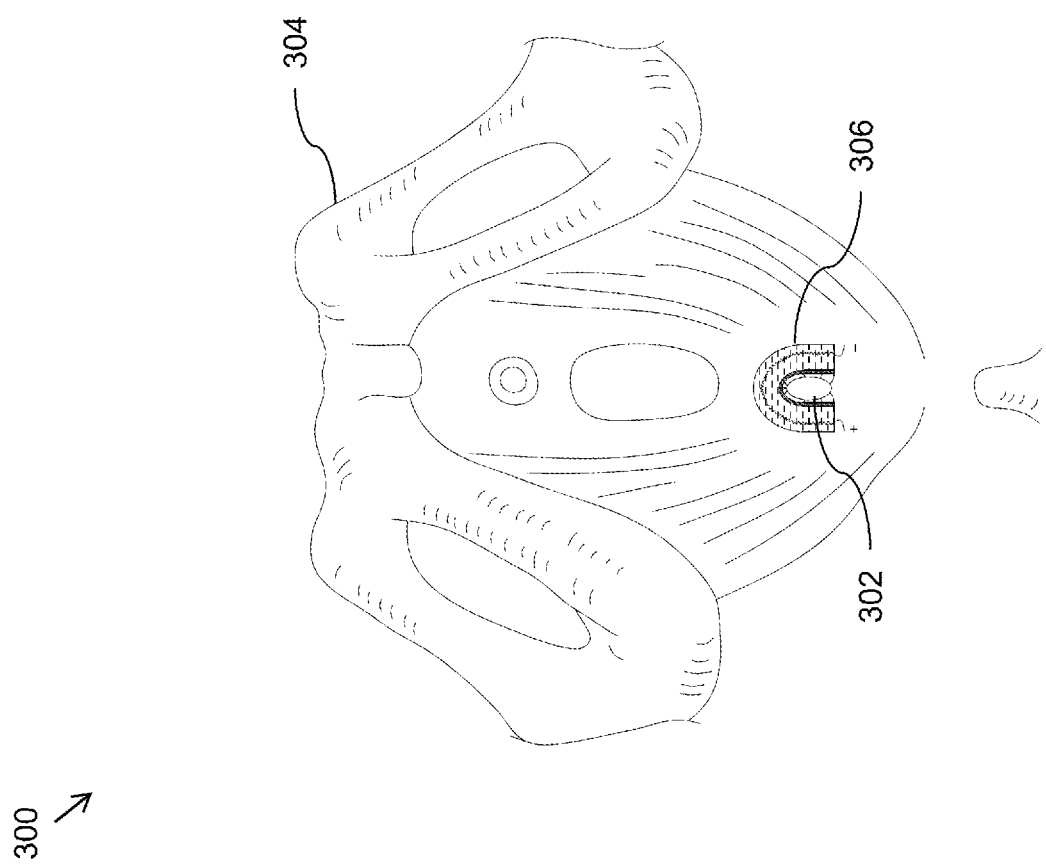
Fig. 3b

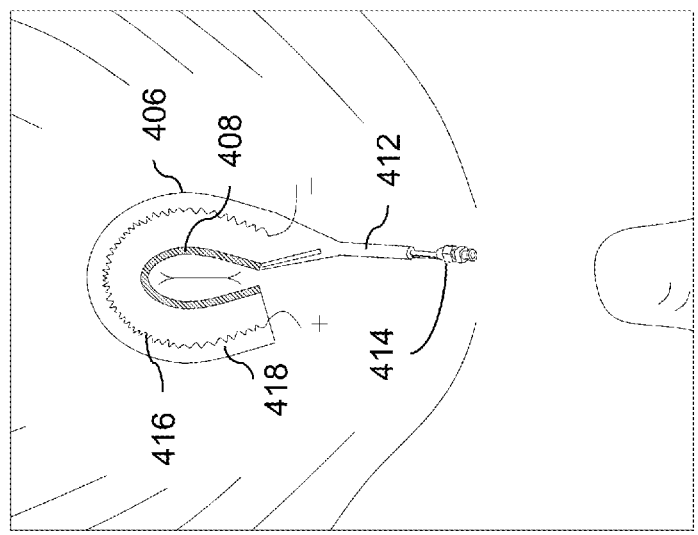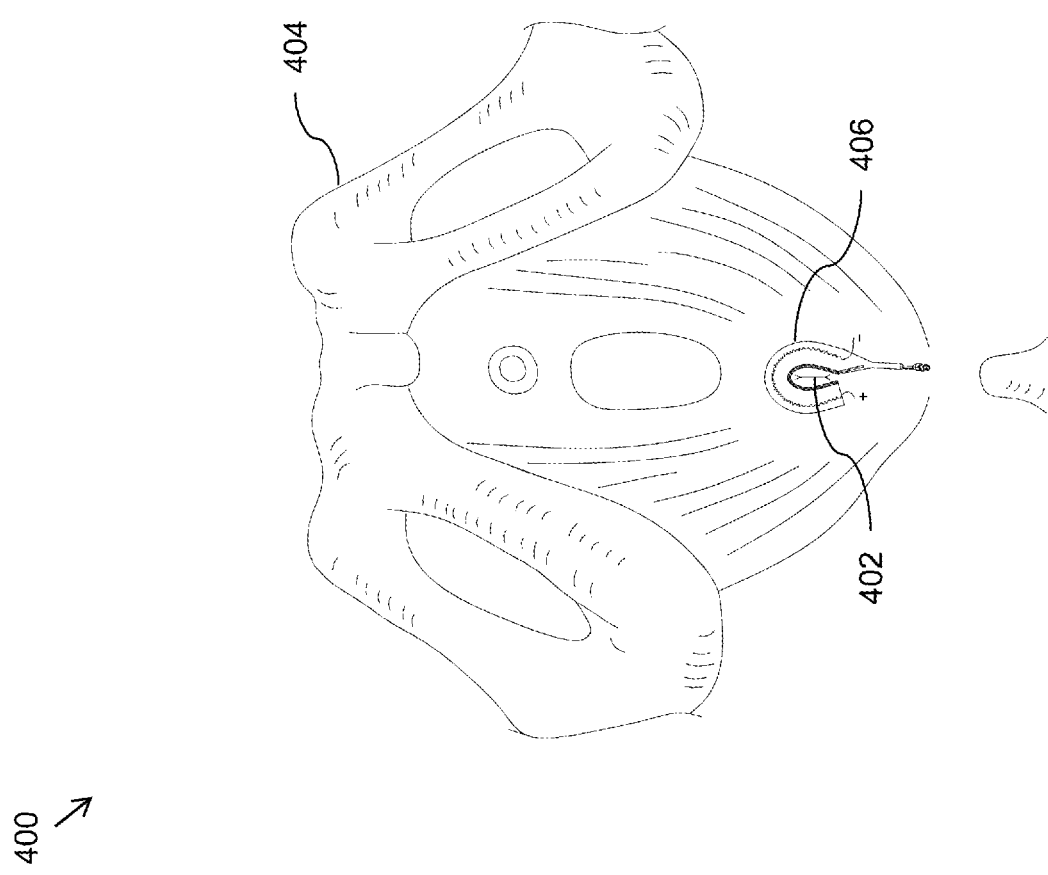
Fig. 4a

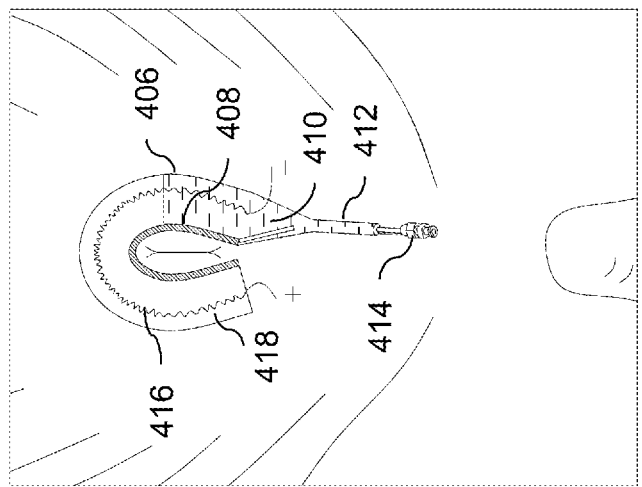
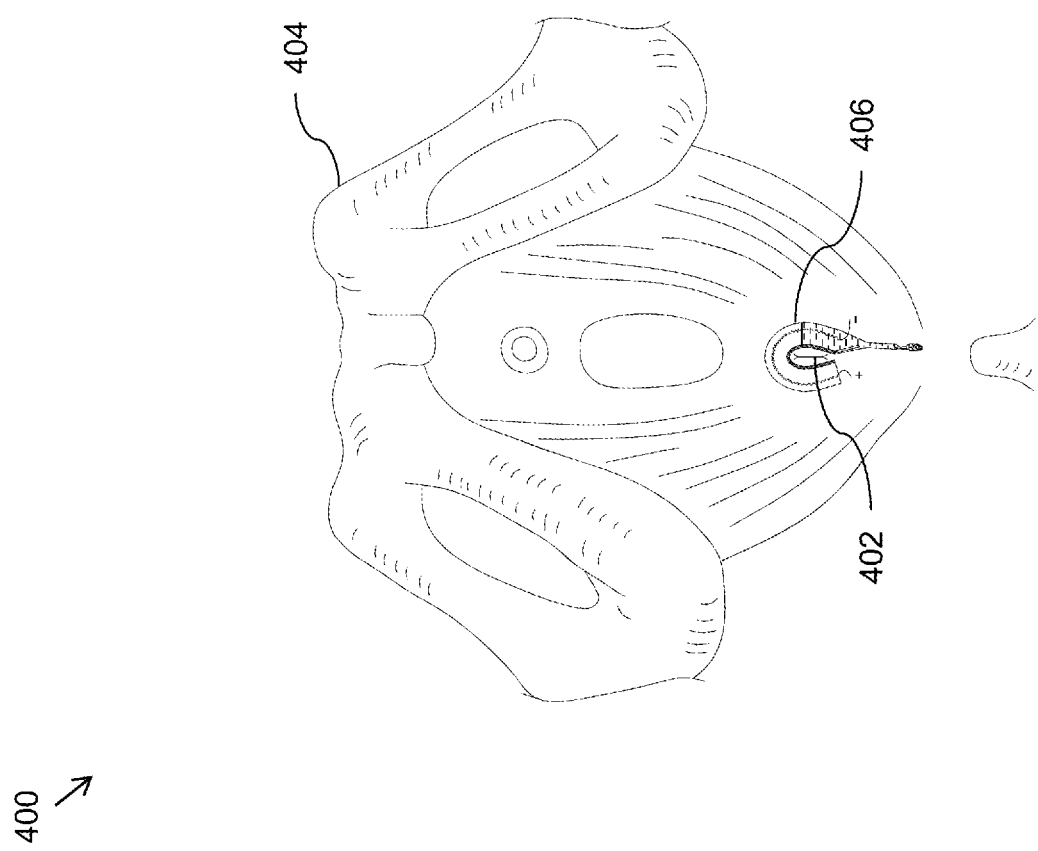
Fig. 4b

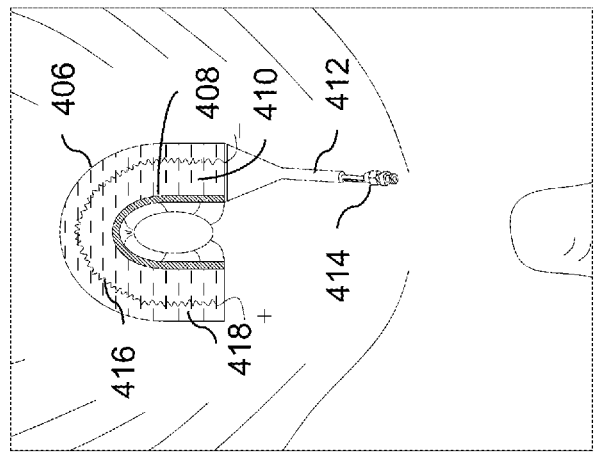
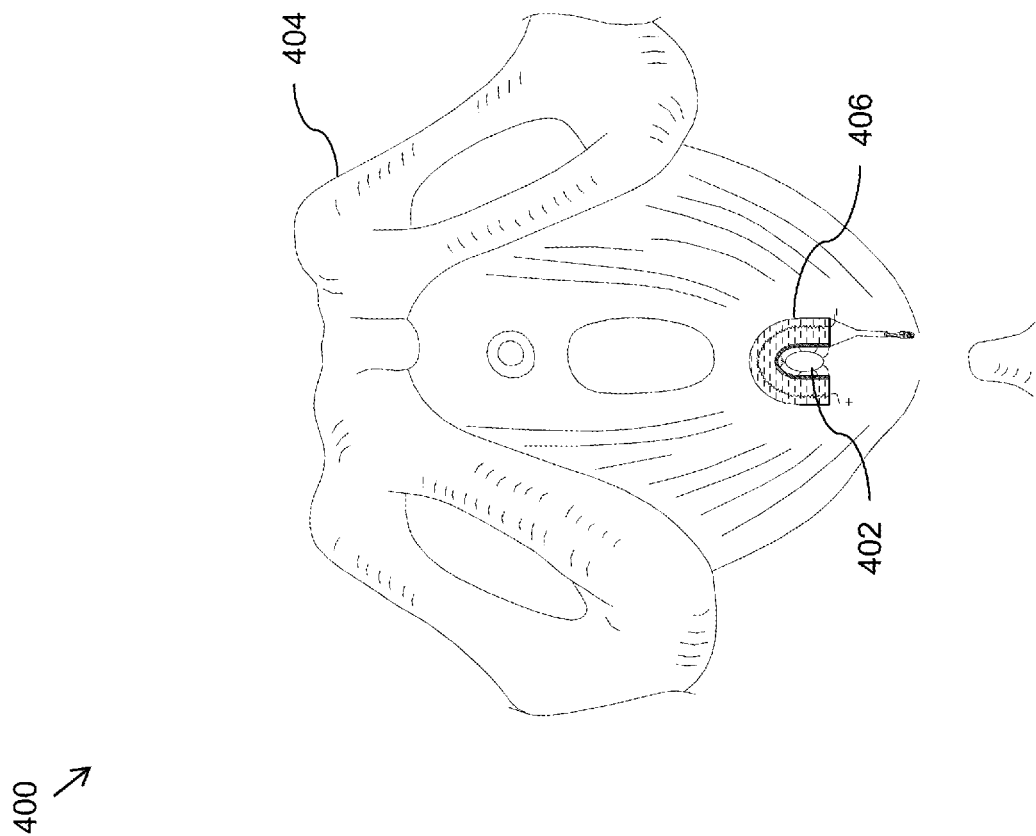
Fig. 4c

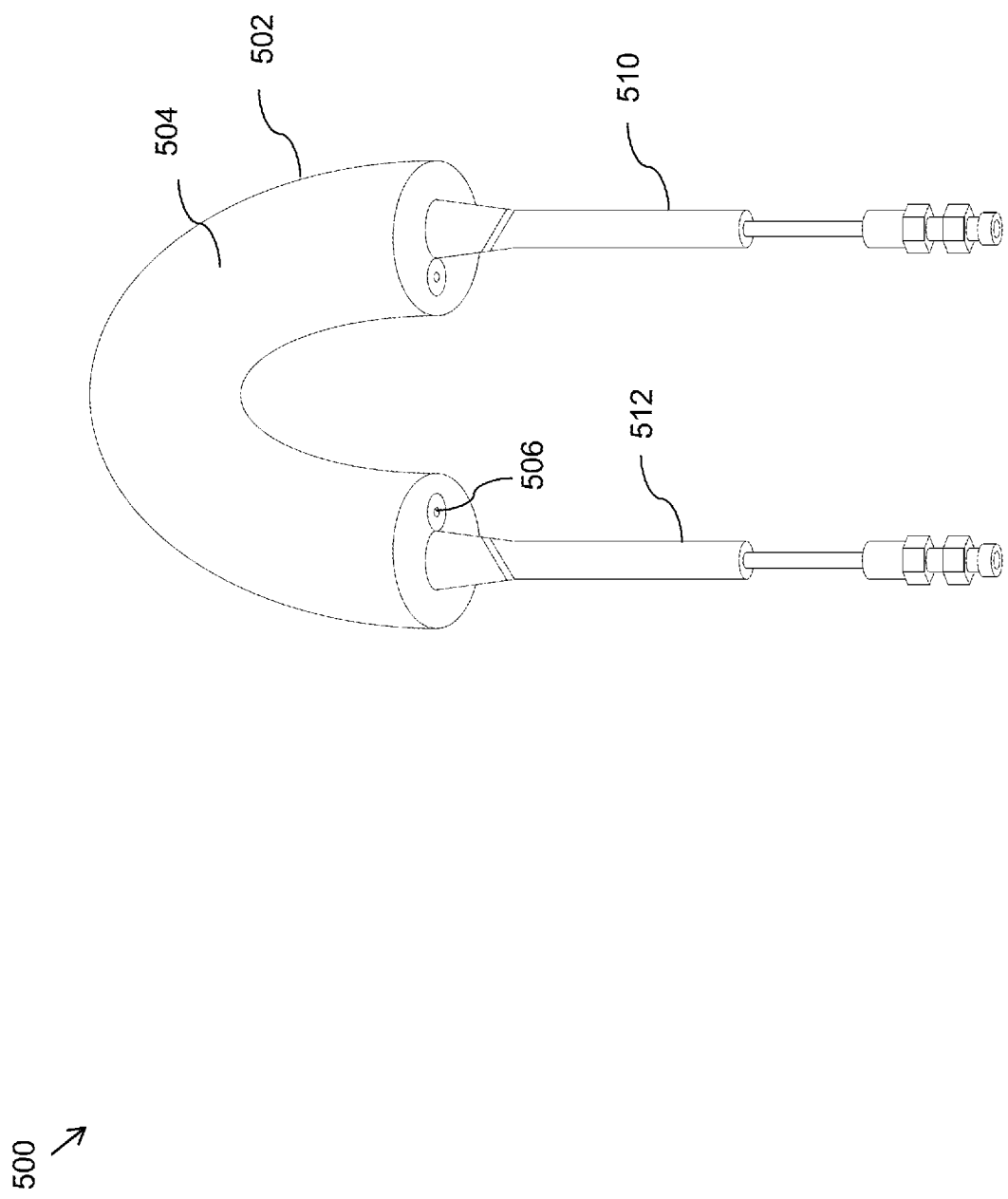

SHAPE MEMORY CONTROLLER

CROSS REFERENCE TO RELATED APPLICATION

This application is a Nonprovisional of, and claims priority to, U.S. Provisional Application No. 61/521,225, filed on Aug. 8, 2011, entitled "SHAPE MEMORY CONTROLLER", which is incorporated by reference herein in its entirety.

BACKGROUND

1. Field

The present invention generally relates to the field of controlling flow of fluids and substances through vessels and openings in a human body, and specifically controlling such a flow using a shape memory apparatus.

2. Description of the Related Art

Human body is composed of a number of vessels, openings, and tubes containing various body fluids and substances. Muscular structures called sphincters are known to surround such openings and orifices of body vessels and passages to maintain the flow of fluids and substances. Any damage or weakness in these sphincters or muscles may result into incontinence, i.e., involuntary discharge of fluids. Incontinence is an ailment affecting a number of men and women worldwide.

A number of methods, procedures, and devices, including rehabilitation and behavior modification, dietary changes, drugs, devices to capture involuntary discharges, and surgical treatments (implants such as artificial sphincters) among others, have been developed for treatment of this problem. The use of artificial sphincters has been widely acknowledged.

Conventional artificial sphincters and implants that occlude the body opening or duct in response to a fluid pressure in the implant are well known. However, use of such exterior fluid pressure may cause pain, skin alteration, thrombosis, and other similar conditions.

Similarly, implants utilizing a manual contraction of a fluid filled collar via a pump, piston, or similar other mechanisms may be physiologically and cosmetically undesirable. In addition, responding to rapid changes in the bladder pressure may be inconvenient for patients as high pressure transients may result in sphincter leakage and subsequently, damage body tissues.

In a similar manner, artificial sphincters constructed of shape memory alloys can also be opened by applying external power or energy, but may cause rupture of the tissues or loss of fluid or pressure and thereby, compromise the effectiveness of the implants over a period of time.

In accordance with the foregoing, there is a need for a method and system that may provide an effective way of controlling the flow of fluids and substances through the body openings such as anus and urethra and thereby, prove useful in conditions such as fecal or urinary incontinence. In addition, there is a need for a method and a system that may be relatively easier to implant, and safe and easy to use.

SUMMARY

An apparatus that may be effective in treating incontinence problems is provided. The apparatus includes an elongate member and a shape memory element. The elongate member is configured to at least partially surround a body lumen and defines a lumen. The shape memory element is disposed of adjacent to the lumen defined by the elongate member. Further, the shape memory element is adapted to change its configuration based on a change in temperature. This change in configuration of the shape memory element causes the apparatus to move between a first configuration and a second configuration.

In an embodiment, an apparatus for selectively opening and closing a body lumen within a patient's body is provided. The apparatus includes an elongate member configured to at least partially surround the body lumen. The elongate member defines a first lumen and a second lumen. The first lumen is configured to receive fluid. Further, the apparatus includes a shape memory element disposed of within the second lumen. The shape memory element is adapted to change configuration based on a change in temperature of the shape memory element. The change in configuration of the shape memory element causes the apparatus to move between a first configuration and a second configuration.

In another embodiment of the present invention, an apparatus for selectively opening and closing a body lumen within a patient's body is provided. The apparatus includes an elongate member configured to at least partially surround the body lumen. The elongate member defines a first lumen and a second lumen. The first lumen is configured to hold fluid. Further, the apparatus includes a shape memory element disposed of within the second lumen. The shape memory element is adapted to change configuration based on a change in temperature of the shape memory element. The change in configuration of the shape memory element causes the apparatus to move between a first configuration and a second configuration.

In yet other embodiment of the present invention, a method of selectively opening and closing a body lumen within a patient's body is provided. The method includes disposing of a device within the patient's body to at least partially surround the body lumen. The device has a first temperature and includes a shape memory element adapted to change configuration based on a change in temperature. Further, the method includes introducing fluid into the elongate member such that the fluid has a second temperature different than the first temperature. The difference in temperature facilitates the change in configuration of the shape memory element to cause the device to move between a first configuration and a second configuration.

In still another embodiment of the present invention, a method of selectively opening and closing a body lumen within a patient's body is provided. The method includes disposing of a device filled with fluid within the patient's body to at least partially surround the body. The fluid is at a first temperature. The device further includes a shape memory element adapted to change configuration based on a change in temperature. Further, the method includes changing the temperature of the fluid to a second temperature such that a change in the fluid temperature causes a change in the configuration of the shape memory element to cause the device to move between a first configuration and a second configuration.

BRIEF DESCRIPTION OF THE FIGURES

The invention and the following detailed description of certain embodiments thereof may be understood with reference to the following figures:

FIG. 1 is a schematic diagram of an apparatus for selectively opening and closing a body lumen within a patient's body, in accordance with an embodiment of the present invention;

FIGS. 3a and 3b schematically illustrate placement of an apparatus for selectively opening and closing a body lumen disposed of within a pelvic region of a patient, in accordance with an embodiment of the present invention;

FIGS. 4a, 4b, and 4c schematically illustrate placement of an apparatus for selectively opening and closing a body lumen disposed of within a pelvic region of a patient, in accordance with another embodiment of the present invention.

FIGS. 5a and 5b are a cross-sectional and a perspective view of an apparatus, respectively, including a first lumen and a second lumen, in accordance with an embodiment of the present invention;

DETAILED DESCRIPTION

Figure 2A:
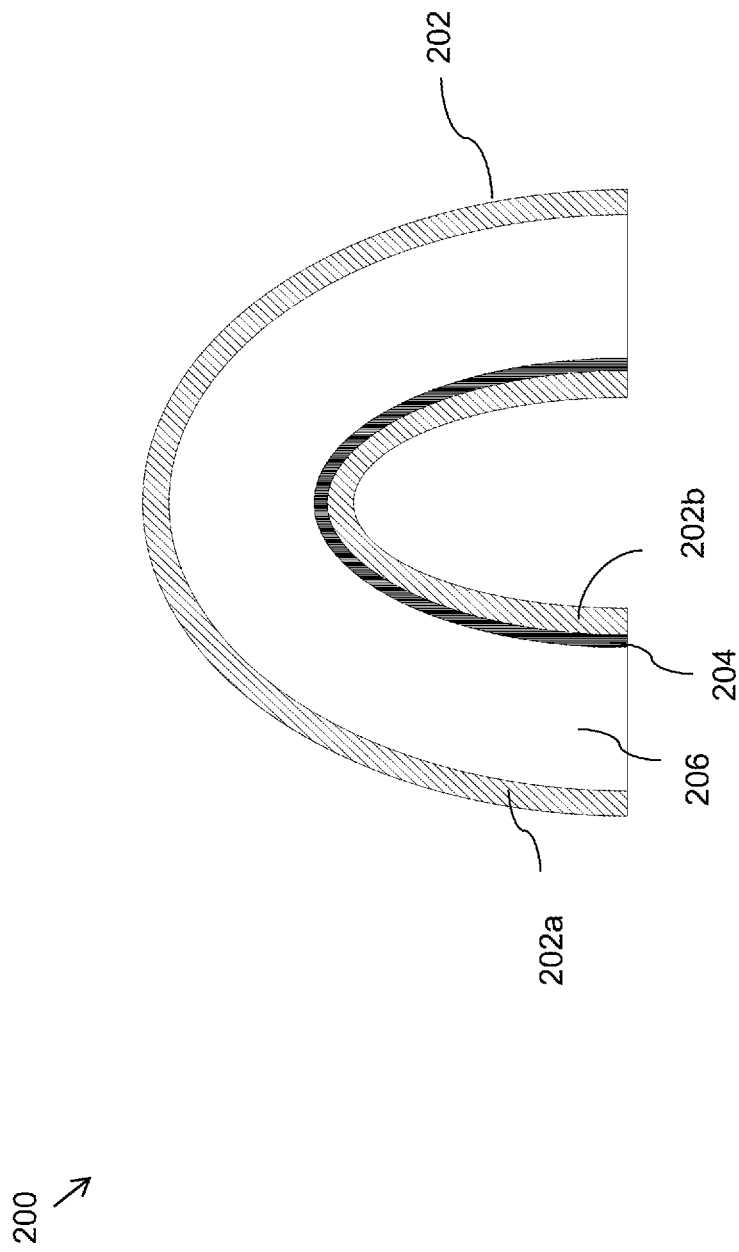
FIGS. 2a and 2b are a cross-sectional and a perspective view of an apparatus, respectively, for selectively opening and closing a body lumen within a patient's body, in accordance with an embodiment of the present invention.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having," as used herein, are defined as comprising (i.e., open transition). The term "coupled" or "operatively coupled," as used herein, is defined as connected, although not necessarily directly and mechanically. The term "configured," as used herein, is defined as designed, functionally or structurally.

The term operator described in relation to various devices, apparatuses, and components as discussed in the subsequent text of the present invention may be a surgeon, a physician, a nurse, a doctor, a technician, or the like, who may perform the procedure of selectively opening and closing a body lumen within a patient's body. The patient may be a human female, a human male, or any other mammal.

The present invention relates to devices and methods for affecting selective opening and closing of the body lumens, channels, openings, ducts, cavities, and the like (hereinafter referred to as the body lumens), and specifically for the treatment of incontinence. The body lumens are responsible for controlling the flow of fluids and substances inside a patient's body. Typically, the flow of fluids and substances inside the patient's body is controlled and maintained by muscles called sphincters that surround the body lumens and constrict or relax depending on the physiological functioning of the body. For example, two sphincters (internal and external anal sphincters) at the anus control the release of feces from the body. Similarly, a urethral sphincter controls the release of urine from the body. However, a number of factors such as muscle or nerve damage, diseases, drugs, dietary, and the like may result in dysfunctioning of these sphincters and subsequently lead to incontinence (inability to control the flow of fluids and substances). The present invention provides systems and methods to address these aspects.

FIG. 1 is a schematic diagram of an apparatus 100 that may be used for selectively opening and closing a body lumen within a patient's body, in accordance with an embodiment of the present invention. The apparatus 100 may be disposed of within the patient's body. The body lumen may be any opening or duct that permits flow of fluids and substances. For example, the body lumen can be an anal opening that allows feces to pass through the patient's body.

The apparatus 100 includes an elongate member 102. In an embodiment, the elongate member 102 is configured to at least partially surround the body lumen such that it holds the body lumen and the surrounding muscles as a clamp. In such a scenario, the elongate member 102 may be designed as a horse-shoe structure. Similarly, in another embodiment, the elongate member 102 may be designed as a ring that completely surrounds the body lumen.

In accordance with various embodiments of the present invention, the elongate member 102 defines a lumen. For example, the elongate member 102 may be designed as a hollow or tubular structure having a lumen inside. In embodiments, the elongate member 102 may be in an expanded/open configuration (i.e., a first configuration) or a collapsed/closed configuration (i.e., a second configuration). As shown in FIG. 1, the apparatus 100 includes a shape memory element 104. The shape memory element 104 is composed of a shape memory material that remembers its original shape and returns to a pre-deformed shape on application of temperature. The type of configuration of the elongate member 102 may depend on the change in configuration of the shape memory element 104.

FIG. 2a is a cross-sectional illustration of an apparatus 200 for selectively opening and/or closing a body lumen within the patient's body, in accordance with an embodiment of the present invention. The apparatus 200 includes an elongate member 202 and a shape memory element 204. The elongate member 202 includes an outer wall 202a and an inner wall 202b. As described earlier in FIG. 1, the elongate member 202 may be designed as a hollow or tubular structure with a lumen 206 inside. The elongate member 202 may be manufactured from a material suitable for implantation in the patient's body. The elongate member 202 may be composed of a biocompatible, formable, and flexible material. The biocompatible materials are used so as to interface with the biological systems such as body tissues without causing sensitization or inflammatory reactions in the body.

Examples of the materials include, but are not limited to, titanium; cobalt; nickel-based alloys; ceramic materials; carbon-based materials such as pyrolytic carbon and vitreous carbon; and plastic moldable materials such as medical grades of polyethylene, polyester, polytetrafluoroethylene (PTFE), expanded PTFE, polypropylene, per-fluorinated polymers, acrylic polymers, polyurethanes, sponge urethane, foamed Teflon, sponge Teflon, titanium or a springy polymer, silicone rubbers, latex, polychloroprene (e.g., neoprene), fully vulcanized thermoplastic rubbers, and thermoplastic elastomers.

In an embodiment, the elongate member 202 may be shaped as a semicircle, horse-shoe, or a ring to at least partially surround the body lumen. Similarly, the elongate member 202 can be a D-shaped cross section, a horseshoe-shaped cylinder with a D-shaped cross section, and any other shapes and cross-sections. In some embodiments, the elongate member 202 can be substantially rectangular, square, oval, elliptical, ring-shaped, and the like. Accordingly, the invention need not be limited to a specific shape of the elongate member 202 and the elongate member 202 can have any geometry, shape, or frame.

In accordance with an embodiment of the present invention, the shape memory element 204 is disposed proximally or adjacent to the lumen 206 defined by the elongate member 202. In certain other embodiments, the shape memory element 204 is embedded in the side walls of elongate member 202. For example, the shape memory element 204 may be embedded in the inner wall 202b of the elongate member 202. The shape memory element 204, also known as a smart metal, memory element or alloy, muscle wire, SME, and the like, is composed of such a material, preferably an alloy that remembers its original shape and returns to a pre-deformed shape on application of temperature. These materials are known to provide a lightweight and feasible alternative to traditional actuators such as hydraulic, pneumatic, and motor-based systems. Examples of the material used for manufacturing shape memory element 204 include alloys of copper-zinc-aluminum-nickel, copper-aluminum-nickel, nickel-titanium, zinc-copper-gold-iron, and the like. In accordance with an embodiment of the present invention, the shape memory element 204 is made of Nitinol (Nickel-Titanium alloy.)

Conventionally, it is known that a memory configuration can be set for Nitinol above a transition temperature, the temperature at which the configuration of the shape memory element 204 changes. During manufacturing, the shape memory element 204 can be held at a specific shape (memory configuration) at the transition temperature for a given time period. At this temperature, the memory configuration of the shape memory element 204 becomes fixed. In case the shape memory element 204 is subjected to a change of temperature, such as heating above the transition temperature, the atoms in the shape memory element 204 will be displaced during deformation and subsequently, return to their pre-deformed condition. Owing to this characteristic of the Nitinol and similar other materials, the shape memory element 204 can be repeatedly deformed and recovered by alteration of temperature.

In accordance with an embodiment of the present invention, the shape memory element 204 has a two-way shape memory effect such that the shape memory element 204 remembers two different shapes corresponding to a low/high temperature. In this case, the shape memory element 204 will remember its high temperature shape on an increase in temperature and when the temperature is decreased, the shape memory element 204 will come back to its cold temperature shape. In certain other embodiments, the shape memory element 204 may have a one-way shape memory effect.

This ability of the shape memory element 204 to change its configuration (based on a change in temperature) can thereby be utilized to cause the apparatus to move between the first configuration and the second configuration and thereby, affect a selective opening and closing of the body lumen, and subsequently in treatment of incontinence. This is explained in detail (below) in conjunction with FIGS. 3 and 4.

The shape memory element 204 can be manufactured in wire, coil, tube, block, slab, and similar other shapes and sizes, in accordance with various embodiments of the present invention.

Further, in an embodiment, the elongate member 202 is configured to receive fluid. Examples of the fluid include, but are not limited to, water, saline water, biocompatible polymers, electro-active polymers, and similar other fluids. In accordance with the embodiments of the present invention, the fluid may be selected such that it is biocompatible and can act as a medium for transferring heat to the shape memory element 204.

Figure 2B:
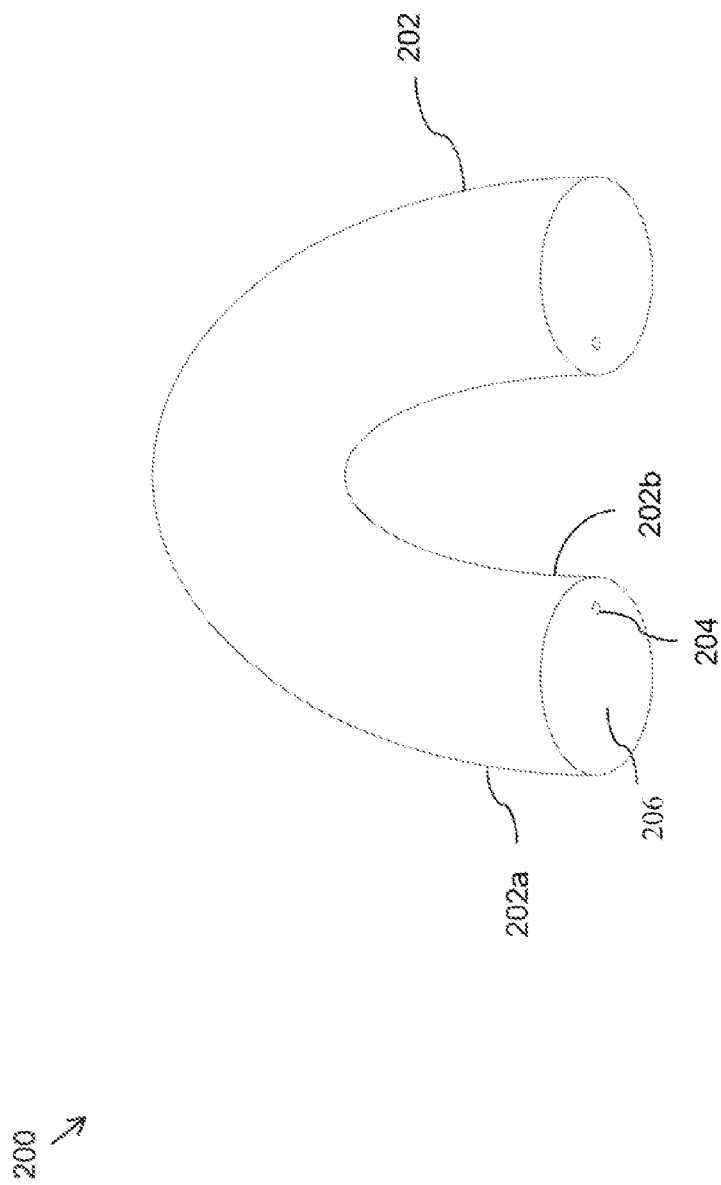

FIG. 2b illustrates the perspective view of the apparatus 200 shown in FIG. 2a, in accordance with an embodiment of the present invention. The apparatus 200 may include a temperature control device (not shown). The temperature control device is configured to change, transfer, and/or control temperature inside the elongate member 202.

In an embodiment of the present invention, the temperature control device may be a heat exchanger. Various types of heat exchanger arrangements can be configured, including a shell and tube type, heating plates, heating/cooling or air coils, spiral or helical tubes and coils, and similar other configurations. For example, the temperature control device may include a number of heating coils that may pass through the apparatus 200. The temperature control device may be provided with electrical connections to facilitate passage of current through the heating coils. The heat generated via the heating coils will be transferred to the fluid that may be introduced inside the elongate member 202, and subsequently to the shape memory element 204 resulting in change in temperature of the shape memory element 204. This change in temperature will cause the shape memory element 204 to change its configuration, cause the apparatus to move between the first configuration and the second configuration, and selectively open or close the body lumen. In another example, the temperature control device may include a heating plate through which current may be passed to heat the fluid and the shape memory element 204.

In accordance with various embodiments of the present invention, the temperature control device may be further provided with sensors (such as thermocouples, Resistance Temperature Detector, i.e., RTD, and the like) for sensing the change and the degree of change in temperature inside the lumen 206 of the elongate member 202. Examples of sensors include, but are not limited to, motion, temperature, vibration, pressure, and proximity sensors.

In other embodiments, the temperature control device may include an output unit (such as electromechanical relay, Solid State Relay, analog/digital output, and the like) that provides a control output (such as safety limit, alarm, heating, or cooling when change in the temperature inside the lumen 206 of the elongate member 202 is detected by the sensors). Further, the temperature control device may include microprocessors or algorithm processing units (such as Proportional Integral Derivative (PID) controllers) to process the information detected by the sensors. For example, the heating coils in the elongate member 202 may be connected to a safety limit controller (on-off type) with a latching output. In case an undesirable temperature level is detected inside the lumen 206 of the elongate member 202, a controller may shut down the current flow and initiate a cooling mechanism (such as passing a coolant) to keep the process within safety limits. An undesirable state (such as temperature greater than a threshold temperature, the temperature above which the apparatus 200 and/or the body tissues may be damaged) within the apparatus 200 may be detected by employing sensors such as temperature sensors inside or outside the apparatus 200.

FIGS. 3a and 3b illustrate the placement of apparatus 300 for selectively opening and/or closing a body lumen, in accordance with an embodiment of the present invention.

FIG. 3a illustrates the apparatus 300 that is placed around a body lumen 302 (shown closed in the figure) within the body of a patient. As shown in FIG. 3a, the apparatus 300 is placed within a pelvic region 304 of a patient. The apparatus 300 includes an elongate member 306 that at least partially surrounds the body lumen 302. The elongate member 306 defines a lumen 314. The apparatus 300 also includes a shape memory element 308. The shape memory element 308 is disposed of adjacent to the lumen 314 defined by the elongate member 306. In some embodiments, the shape memory element 308 may be embedded in the walls of the elongate member 306. Further, the elongate member 306 is configured to hold fluid 310 in the lumen 314. The fluid 310 may be the biocompatible fluid such as a polymer. In an embodiment, the lumen 314 defined by the elongate member 306 may hold water at a first temperature. The first temperature may be at body temperature (i.e., 37 degrees Centigrade or 98.6 degrees Fahrenheit). A first configuration (e.g., V-shape) of the shape memory element 308 is in such a manner that the elongate member 306 and the shape memory element 308 clamp the body lumen 302. In such a configuration of the shape memory element 308, the opening of the body lumen 302 is in a closed, constricted, or an occluded state and does not allow the flow or passage of fluids and substances, such as feces, when the fluid 310 and the shape memory element 308 are at the first temperature.

The apparatus 300 further includes a temperature control device 312 such as a heating coil. The temperature control device 312 is configured to change, transfer, and/or control temperature inside the elongate member 306 by facilitating passage of electric signals for heating or raising the temperature of the coil and subsequently, the fluid 310 inside the elongate member 306. The temperature control device 312 can be connected to electrical terminals (e.g., electrical connections leading to an anode or a cathode outside the patient's body; not shown in the figure) for transmitting/controlling the electric signals. The temperature control device 312 may be further provided with sensors, output unit, and microprocessors.

In accordance with an embodiment of the present invention, the apparatus 300 may be provided with a power source (not shown in the figure) such as power supply lines (ac or dc voltage lines), energy storage devices such as batteries, fuel cells, solar cells, and the like. The energy may be stored (if needed) and may be transferred to the apparatus 300 thereafter to change the temperature of the fluid 310 as well as the shape memory element 308 to cause the apparatus 300 to move between the first configuration and the second configuration. In accordance with various embodiments of the present invention, the first configuration may be an open or expanded configuration and the second configuration may be a closed or collapsed configuration. This movement may selectively open or close the body lumen 302 inside the patient's body. This will be explained in detail later.

When an electric signal (e.g., through an AC power supply) is passed through the temperature control device 312, the temperature control device 312 is energized. By way of conduction, the heat from the temperature control device 312 is passed to the surrounding fluid 310. This heat in turn increases the temperature of the fluid 310 and the shape memory element 308 that is disposed of adjacent to the lumen 314 defined by the elongate member 306. In an embodiment, the shape memory element 308 is embedded in the sidewalls of the elongate member 306. As the temperature increases beyond the transition temperature, the tension between two ends of the shape memory element 308 relaxes and the deformation of the shape memory element 308 to the second configuration (e.g., a U-shape) begins. The configuration of the shape memory element 308 subsequently changes to an open or U-shaped element. This change in configuration also pulls the sidewalls of the elongate member 306. As a result, the apparatus 300 moves from the closed configuration to the open configuration, thereby releasing the opening of the body lumen 302 that was originally caused to be occluded or closed by the apparatus 300. This has been illustrated in conjunction with FIG. 3b. Thereafter, fluids and substances such as feces can be easily passed through the opened body lumen 302.

Likewise, once the feces are passed, the temperature of the fluid 310 and the shape memory element 308 may be decreased such that the tension between two ends of the shape memory element 308 increases and the deformation of the shape memory element 308 back to the first configuration (e.g., V-shape) begins. In embodiments, the temperature of the fluid 310 may be decreased by either stopping/minimizing the flow of electrical signals to the temperature control device 312 or by passing a coolant through the lumen 314 of the elongate member 306. Examples of the coolant may include cold water, air, and any other biocompatible fluid. The coolant may have high thermal capacity and low viscosity; and may be non-toxic, and chemically and biologically inert. The change in configuration of the shape memory element 308 to V-shape pushes the sidewalls of the elongate member 306. As a result, the apparatus 300 changes from open configuration to the closed configuration, thereby constricting the opening of the body lumen 302 that was earlier caused to be opened by the apparatus 300.

FIGS. 4a, 4b, and 4c illustrate the placement of the apparatus 400 for selectively opening and/or closing a body lumen 402, in accordance with another embodiment of the present invention.

Referring to FIG. 4a, the apparatus 400 is placed within a pelvic region 404 of a patient. The apparatus 400 includes an elongate member 406 configured to at least partially surround the body lumen 402. The elongate member 406 defines a lumen 418. The apparatus 400 also includes a shape memory element 408 that is disposed of adjacent to the lumen 418 defined by the elongate member 406. In embodiments, the shape memory element 408 may be embedded in the elongate member 406. The shape memory element 408 is adapted to change the configuration based on a change in temperature of the shape memory element 408. This change in configuration of the shape memory element 408 may cause the apparatus 400 to move between a first configuration and a second configuration. As a result, the body lumen 402 may be selectively opened and/or closed.

In accordance with an embodiment of the present invention, the lumen 418 of the elongate member 406 is configured to receive fluid such as water, biocompatible polymers, and the like. This embodiment specifically discloses a scenario wherein the fluid may be later introduced inside the apparatus 400 and accordingly the elongate member 406, which may not necessarily hold the fluid.

The configuration or shape of the elongate member 406 and the shape memory element 408 is in such a manner that they are at a first temperature (e.g., the body temperature) and clamp the body lumen 402. In such a configuration of the shape memory element 408, the opening of the body lumen 302 is in a closed, constricted, or an occluded state and does not allow the flow or passage of the fluids and substances such as feces, when the shape memory element 408 is at the first temperature.

In case there is a need for fluids and/or substances to pass through the opening of the body lumen 402, such as for excretion of feces (through the anus) or fluid 410 (shown in FIG. 4b), which is at a different temperature than the temperature of the shape memory element 408, is passed or introduced through the elongate member 406.

In an embodiment, the fluid 410 is hot, warm, or cold water. The temperature of the fluid 410 is the second temperature, in accordance with various embodiments of the present invention.

The apparatus 400 is provided with an insertion device 412 to introduce the fluid 410 (as shown in FIGS. 4b and 4c) inside the lumen 418. Examples of the insertion device 412 include, but are not limited to, a pump, a syringe, a dosing system, a jet, an injector, an infusion pump, an osmotic pump, a pen injector, and similar other devices that can be used to introduce the fluid 410 inside the elongate member 406.

As illustrated in FIGS. 4a, 4b, and 4c, the insertion device 412 may include a valve 414 to facilitate introduction and/or control of the fluid 410 inside the lumen 418 of the elongate member 406. Examples of the valve 414 include, but are not limited to, ball valve, butterfly valve, check valve, diaphragm valve, gate valve, globe valve, piston valve, plug valve, flow control valve, leaf valve, rotary valve, disc valve, swirl valve, and regulator. In another embodiment, the insertion device 412 may include a plurality of valves similar to the valve 414.

As shown in FIGS. 4b and 4c, the fluid 410 having a temperature higher (the second temperature) than the temperature inside the lumen 418 of the elongate member 406 is introduced through the insertion device 412. For example, the fluid 410 at a temperature of 46 degrees Centigrade (114.8 degrees Fahrenheit) is introduced inside the elongate member 406 having a temperature of 37 degrees Centigrade (98.6 degrees Fahrenheit).

In certain embodiments, the fluid 410 may be heated to or above the transition temperature of the shape memory element 408 by a temperature control device 416, such as a heating coil, prior to introduction through the insertion device 412. As discussed earlier in conjunction with FIGS. 2, 3a, and 3b, electrical connections can be provided therein to facilitate passage of electrical signals or current through the temperature control device 416. In other embodiments, wireless heating may be employed to heat the fluid 410.

The fluid 410, on being introduced to the elongate member 406, transfers its heat to the sidewalls of the elongate member 406 and subsequently, to the shape memory element 408 that may have a transition temperature of 46 degrees Centigrade (114.8 degrees Fahrenheit.) As a result of the increase in temperature of the shape memory element 408, a change in the configuration of the shape memory element 408 is initiated. As a result, the tension between two ends of the shape memory element 408 is relaxed, and the deformation of the shape memory element 408 to a second configuration (e.g., U-shape) begins. This change in configuration also pulls the sidewalls of the elongate member 406, thereby releasing the opening of the body lumen 402 that was originally caused to be occluded or closed by the elongate apparatus 400. This has been illustrated in conjunction with FIGS. 4b and 4c. Thereafter, the fluids and substances such as feces can be easily passed through the opened body lumen 402.

Further, once the feces are passed, the temperature of the shape memory element 408 can be decreased such that the tension between two ends of the shape memory element 408 increases and the deformation of the shape memory element 408 back to the first configuration (V-shape) begins. In embodiments, the temperature of the shape memory element 408 may be decreased by discharging or emptying the fluid 410 from the elongate member 406, and allowing the elongate member 406 and the shape memory element 408 to return to the first temperature. In other embodiments, another fluid such as a coolant may be passed through the elongate member 406 to decrease the temperature of the shape memory element 408. Examples of the coolant may include cold water, air, and any other biocompatible fluid. The change in the configuration of the shape memory element 408 from U-shape to V-shape pushes the sidewalls of the elongate member 406, causing the apparatus to close. As a result, the opening of the body lumen 402 is constricted again, which was earlier caused to be opened by the apparatus 400.

Figure 5A:
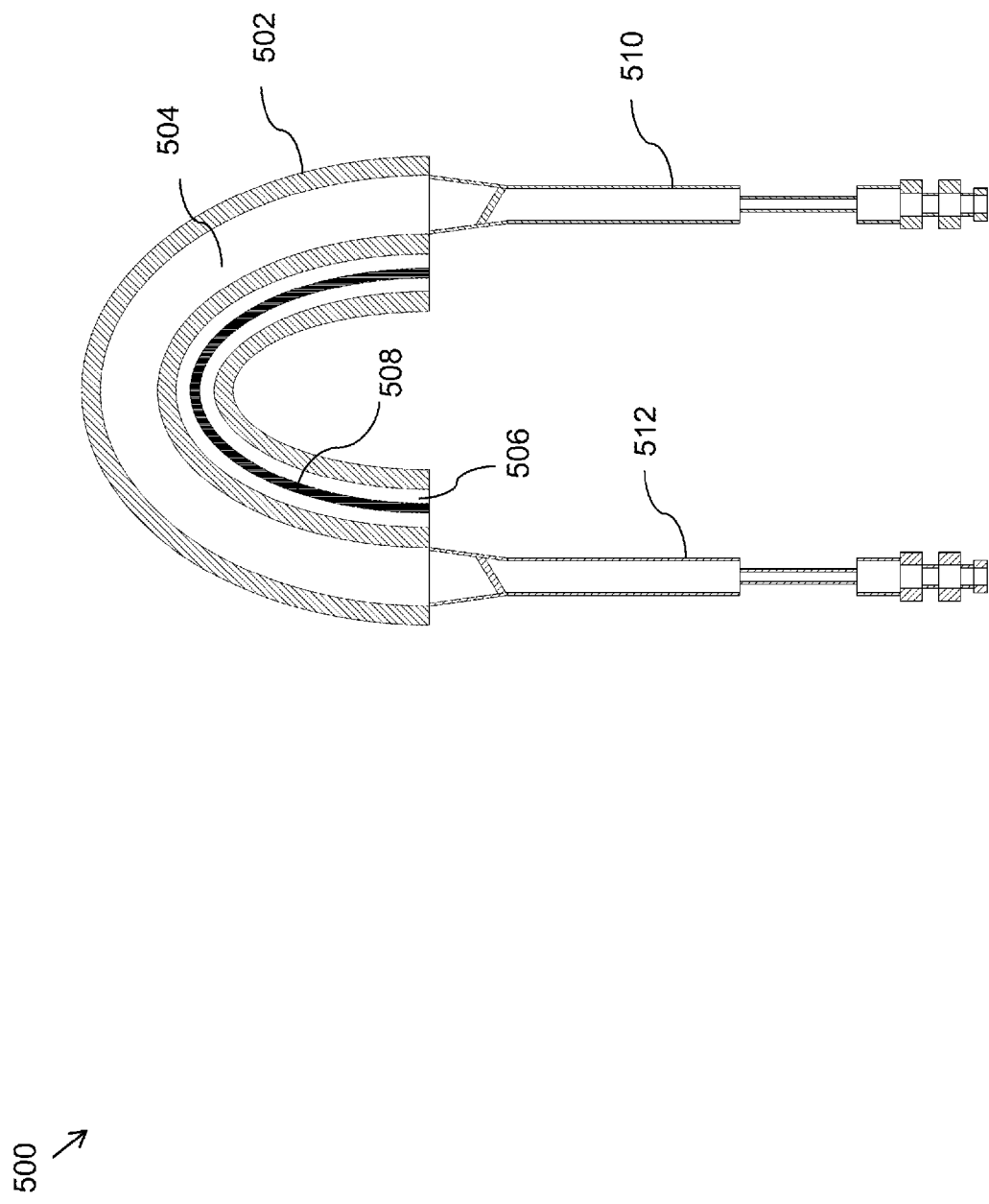

FIG. 5a is a cross-sectional view of an apparatus 500 for selectively opening and closing a body lumen within a patient's body, in accordance with an embodiment of the present invention. The apparatus 500 includes an elongate member 502. The elongate member 502 is configured to at least partially surround the body lumen. Further, the elongate member 502 defines or includes a first lumen 504 and a second lumen 506. In embodiments, the first lumen 504 and the second lumen 506 inside the elongate member 502 may be created by using a wall or barrier, or similar other structures composed of biocompatible material that may partition the elongate member 502.

In other embodiments, the elongate member 502 may be a first elongate member and may be configured to hold a second elongate member. In such a case, the first elongate member may define or include the first lumen 504 and the second elongate member may define or include the second lumen 506.

Referring to FIG. 5a, the first lumen 504 is configured to receive and/or hold fluid. As discussed earlier in conjunction with FIGS. 2, 3, and 4, the fluid may be water or any other biocompatible fluid. The apparatus 500 also includes a shape memory element 508 that is disposed of adjacent to or within the second lumen 506. In accordance with the embodiments of the present invention, the first lumen 504 and the second lumen 506 have a first temperature and a second temperature, respectively. In certain embodiments, the second temperature may be the transition temperature of the shape memory element 508. Further, the shape memory element 508 is adapted to change its configuration based on a change in temperature of the shape memory element 508.

As shown in FIG. 5a, the second lumen 506 may isolate the shape memory element 508 from the fluid in the first lumen 504. This is specifically useful in case the fluid may affect the properties of the shape memory element 508.

In some embodiments, the apparatus 500 also includes a temperature control device (not shown in the figure) such as a heating coil to change, transfer, and/or control temperature inside the elongate member 502 by facilitating passage of electric signals for heating or raising the temperature of the coil and subsequently, the fluid inside the elongate member 502. The temperature control device may be further connected to electrical terminals (e.g., electrical connections leading to an anode or a cathode outside the patient's body but not shown in the figure) for transmitting/controlling the electric signals. In some embodiments of the present invention, the temperature control device may be provided outside the first lumen 504.

FIG. 5b is a perspective illustration of the apparatus shown in FIG. 5a, in accordance with an embodiment of the present invention. Referring to the FIGS. 5a and 5b, the apparatus 500 may include a first insertion device 510 to introduce the fluid through a first side of the elongate member 502, and a second insertion device 512 to facilitate either introduction or discharge of the fluid and/or a coolant through a second side of the elongate member 502. Examples of the first and second insertion devices 510 and 512 include, but are not limited to, a pump, a syringe, a dosing system, a jet, an injector, an infusion pump, an osmotic pump, a pen injector, and similar other devices that can be used to introduce fluid and/or coolant inside the elongate member 502. For ease of reference, the description hereinafter considers only the first insertion device 510.

Initially, the first lumen 504 may be at the normal body temperature. At this stage, the shape memory element 508 inside the second lumen 506 is at a first temperature. In one embodiment, this first temperature may be a normal body temperature. The shape memory element 508 is in a first configuration (e.g., V-shape) and clamps the opening of the body lumen in such a manner that fluids or substances cannot pass through the opening.

In embodiments where the first lumen 504 holds the fluid, the current is passed via the heating coils to heat the fluid. Heat from the fluid in the first lumen 504 is transferred to the sidewalls of the second lumen 506 and thereafter to the shape memory element 508. Above the transition temperature, the shape memory element 508 changes its configuration from the first configuration (V-shape) to a second configuration (e.g., U-shape) such that the opening of the body lumen changes from a constricted to an open state. Accordingly, the fluids and substances such as feces are passed through the opened body lumen. Once the fluids and substances are passed, the temperature of the shape memory element 508 can be decreased by allowing the fluid to cool, or by discharging the fluid from the elongate member 502, or by introducing a coolant in the elongate member 502 such that the shape memory element 508 returns to its first temperature. This change in temperature will again change the configuration of the shape memory element 508 from the second configuration (U-shape) to the first configuration (V-shape) and thereby, constrict the opening of the body lumen again, which was earlier caused to be opened by the elongate member 502.

In embodiments where the first lumen 504 receives fluid from outside the elongate member 502, current may be passed once the fluid has been introduced via the first insertion device 510. Although the embodiments of the present invention have been explained using a temperature control device, the apparatus 500 may work without a temperature control device as well. In such a case, the fluid may be heated outside the apparatus 500 prior to introduction in the first lumen 504 via the first insertion device 510.

Figure 6:
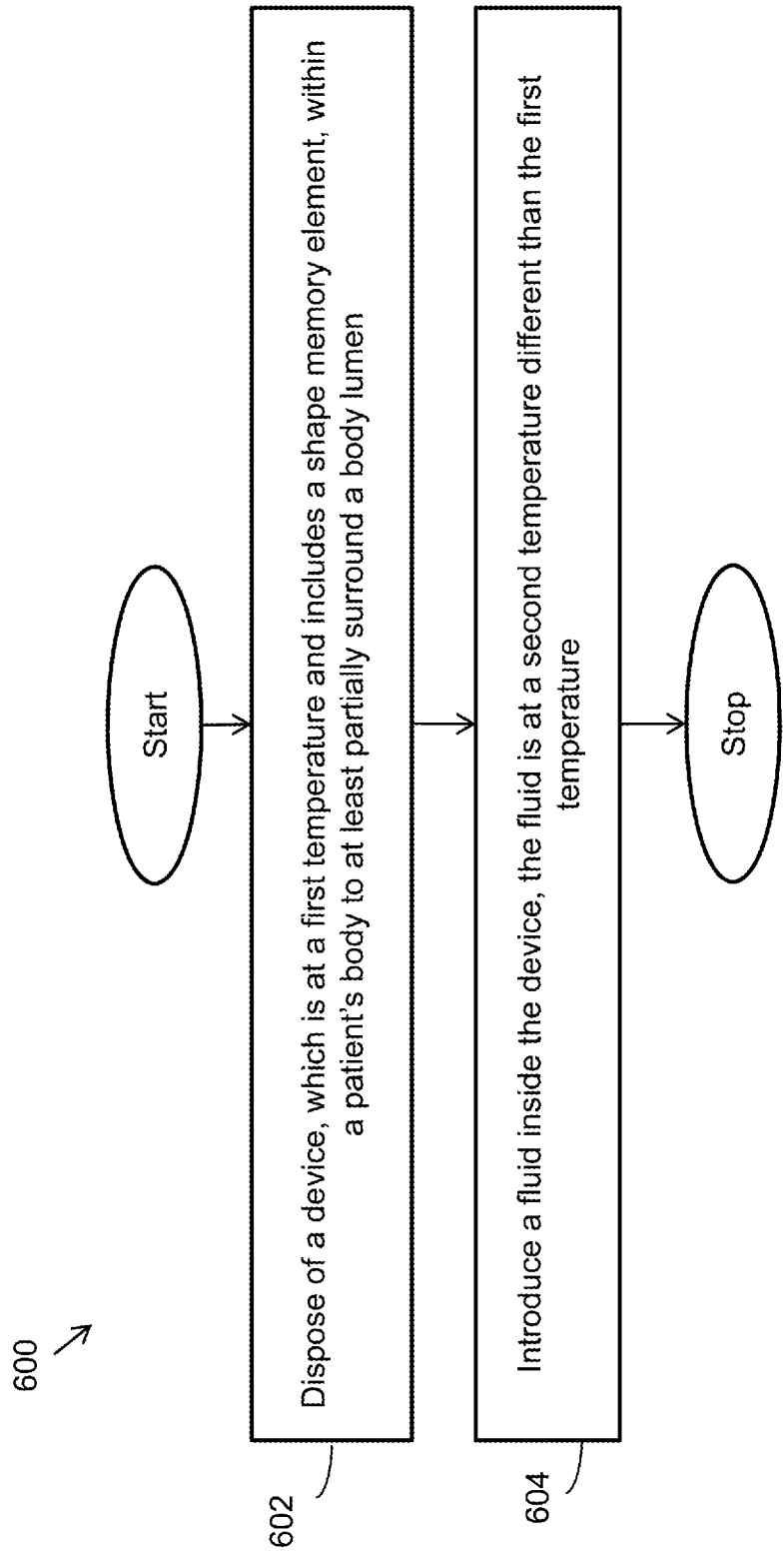
FIG. 6 is a flowchart illustrating a method of selectively opening and closing a body lumen within a patient's body, in accordance with an embodiment of the present invention.

FIG. 6 is a flowchart illustrating a method 600 of selectively opening and closing a body lumen within a patient's body, in accordance with an embodiment of the present invention. As illustrated in FIG. 6, the method 600 includes a step 602. At step 602, the operator may dispose of a device or an apparatus (such as an apparatus described in conjunction with FIGS. 1, 2, 3a, 3b, 4a, 4b, 4c, and 5) within the patient's body to at least partially surround the body lumen. In embodiments, the device may be an elongate member. The device has a first temperature and includes a shape memory element (such as the shape memory element described in conjunction with FIGS. 1, 2, 3a, 3b, 4a, 4b, 4c, and 5). In an embodiment of the present invention, the first temperature is the normal body temperature. The shape memory element is adapted to change its configuration based on the changes in temperature.

In accordance with various embodiments of the present invention, known methods and surgical processes for placement of the device or the apparatus within the patient's body may be employed. In embodiments, the device may be disposed of adjacent to a portion of the body lumen. In this case, the operator can make bodily incisions in perineum, anteriolateral, posteriolateral, or lateral locations with respect to a body part such as an anus of the patient. The operator may insert a surgical tool through any of the incisions and hold the device around the body lumen firmly. The incisions can finally be closed and sutured. After being placed, the device may take the form similar to a ring or a loop.

In case the device has certain support structures such as arms, they may be fixed to any other anterior or posterior skin incision, the coccyx bone, and the like. For example, the arms can be sutured to skin proximally or adjacent to the incisions. In some embodiments, the incision may be a vaginal incision. In other embodiments, the incision may be a buttock incision made on a right buttock and/or a left buttock. In still other embodiments, the incision may be a perennial incision made in the perennial body. Similarly, the incision can be made at various possible locations for facilitating the insertion of the device within the patient's body.

In some embodiments of the present invention, the device may be designed structurally or functionally as a ring with a slot to facilitate its implantation in the body of the patient.

The method 600 flows to step 604 where a fluid (such as water, saline water, or biocompatible fluid) is introduced inside the device. The fluid is at a second temperature different than the first temperature of the device. In an embodiment of the present invention, the second temperature is higher than the first temperature. In another embodiment, the second temperature is a transition temperature associated with the shape memory element. The difference between the first temperature and the second temperature facilitates change in the configuration of the shape memory element to cause the device to move from a closed configuration to an open configuration. For example, at the first temperature of the device, the shape memory element is at a first configuration (V-shape) such that the device and the shape memory element clamp the opening of the body lumen and do not allow any fluid or substance to pass through the body lumen. When a fluid is at the second temperature, i.e., higher than the first temperature of the shape memory element, and the device is introduced, the heat from the fluid increases the temperature of the shape memory element to the second temperature causing the shape memory element to change its configuration to a second configuration (U-shape). The U-shape configuration of the shape memory element releases the opening of the body lumen, thereby allowing the fluids and substances to pass through the opening of the body lumen. Once the fluids and substances are passed, the temperature of the shape memory element can again be decreased by adopting the various methods described above. A decrease in temperature will be followed with a change in configuration of the shape memory element from the U-shape to the V-shape. As a result, the opening of the body lumen will again be constricted by the shape memory element and the device will return to its original shape.

Figure 7:
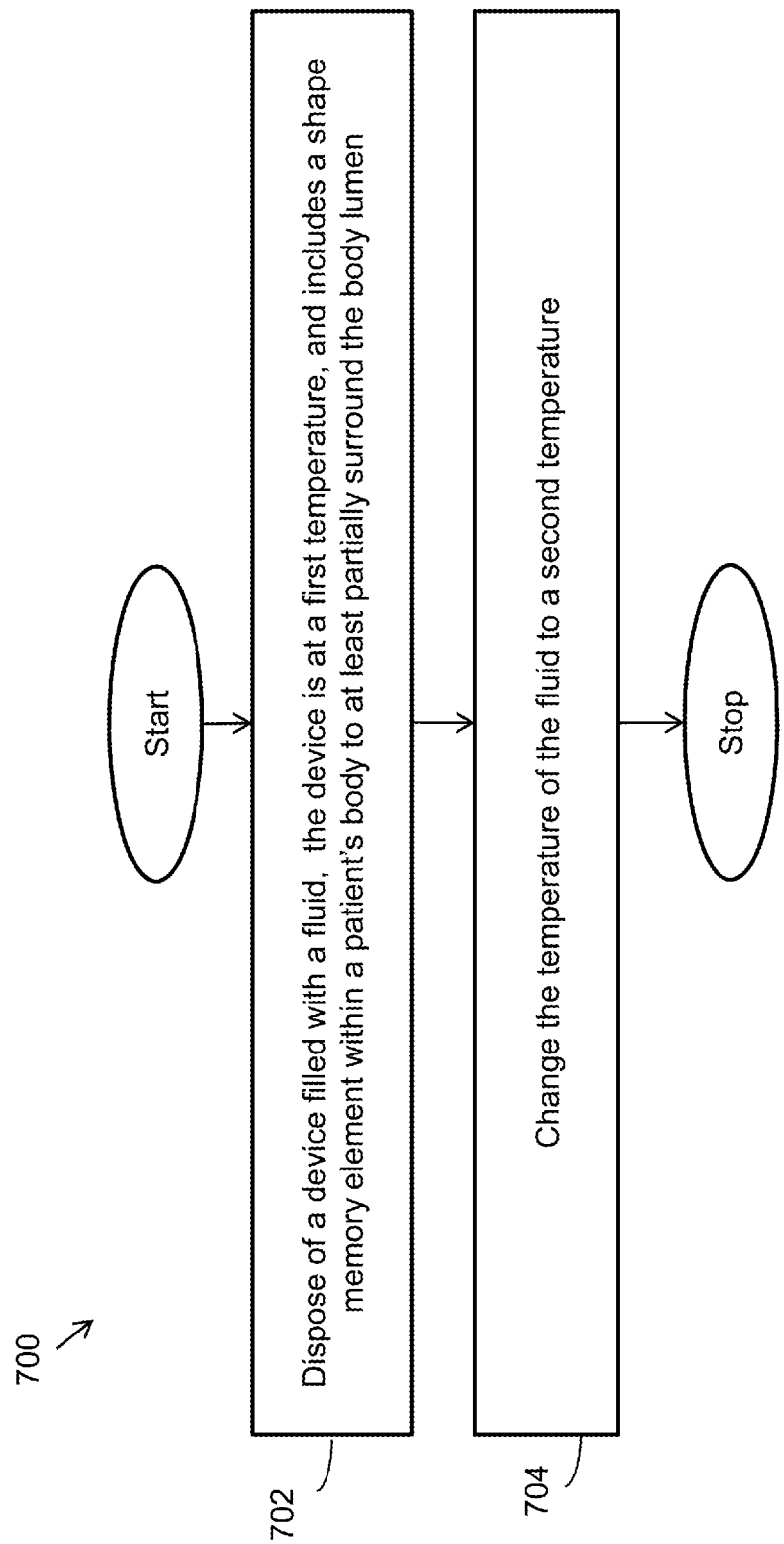
FIG. 7 is a flowchart illustrating a method of selectively opening and closing a body lumen within a patient's body, in accordance with another embodiment of the present invention.

Referring to FIG. 7, a method 700 of selectively opening and closing a body lumen within a patient's body is illustrated, in accordance with another embodiment of the present invention. At step 702, a device or an apparatus (such as an apparatus described in conjunction with FIGS. 1, 2, 3a, 3b, 4a, 4b, 4c, and 5) filled with a fluid is disposed of within the patient's body to at least partially surround the body lumen (e.g., an anal opening). In embodiments, the device may be an elongate member. As discussed earlier in conjunction with FIG. 6, the device may be disposed of adjacent to a portion of the body lumen. In this case, an operator can make incisions in perineum, anteriolateral, posteriolateral, or lateral locations with respect to a body part such as an anus of the patient. The operator may insert a surgical tool through any of the incisions and hold the device around the body lumen firmly. The incisions can be finally closed and sutured. After being placed, the device may take the form similar to a ring or a loop.

In case the device has certain support structures such as arms, they may be fixed to any other anterior or posterior skin incisions, the coccyx bone, and the like. For example, the arms can be sutured to skin proximally or adjacent to the incisions. In some embodiments, the incision may be a vaginal incision. In other embodiments, the incision may be a buttock incision made on a right buttock and/or a left buttock. In still other embodiments, the incision may be a perennial incision made in the perennial body. Similarly, the incision can be made at various possible locations for facilitating the insertion of the device within the patient's body.

In some embodiments of the present invention, the device may be designed structurally or functionally as a ring with a slot to facilitate implantation in the body of the patient.

Referring to step 702, the fluid inside the device is at a first temperature. In an embodiment, the first temperature may be a normal body temperature. Examples of fluid include, but are not limited to, water, saline water, and biocompatible polymers.

The device filled with fluid further includes a shape memory element. The shape memory element is adapted to change its configuration based on a change in temperature.

The method 700 proceeds to step 704. At step 704, the temperature of the fluid is changed to a second temperature. In an embodiment, the second temperature is different than the first temperature. In accordance with an embodiment of the present invention, this change in temperature may be caused by employing a temperature control device such as a heating coil. The temperature control device may be further provided with electrical connections to facilitate passage of current through the heating coils. The heat generated via the heating coils will be transferred to the fluid to increase the fluid's temperature from the first temperature to the second temperature.

In other embodiments of the present invention, a coolant or a heat reducing mechanism (such as cooling by air) may be employed inside the device such that the second temperature is lower than the first temperature.

In yet other embodiments, the second temperature may be either equal to or higher than the transition temperature of the shape memory element.

Accordingly, the change in fluid temperature causes a change in the configuration of the shape memory element and subsequently, the device. This results in selective opening and/or closing of the body lumen that is at least partially surrounded by the elongate member and the shape memory element. Thereafter, the fluid and substances such as urine and feces can be easily voided from the body, which facilitates to control the incontinence problem. Once the fluids and substances are discharged from the patient's body, the temperature of the fluid and the shape memory element may again be changed such that the shape memory element returns to its original shape and the body lumen opens or closes accordingly.

In some embodiments of the present invention, a control system for controlling the application of heat, voltage, current, and the like, and subsequently the temperature inside the apparatus may be provided. This control system may be further equipped with sensors, feedback units, processors, and other similar units and modules that may facilitate a controlled and automated opening and/or closing of the body lumens using this apparatus.

The apparatus and/or device, as described in accordance with various embodiments of the present invention, may be tied with sutures, staples, adhesives, pins, and the like. In other embodiments, the pressure from body tissues may provide enough support for fixing the apparatus within the patient's body.

The embodiments of the present invention have been explained such that the configuration of a shape memory element changes from a V-shape (collapsed or closed) to a U-shape (expanded or open) configuration corresponding to a closed and an open body lumen upon change in temperature of fluid inside an elongate member, and specifically increase in fluid temperature inside the elongate member. However, a vice-versa configuration, wherein the configuration of the shape memory element changes from a U-shape (expanded or open) to a V-shape (collapsed or closed) configuration corresponding to an open and a closed body lumen upon change in temperature of the fluid inside the elongate member, and specifically increase in fluid temperature inside the elongate member may be possible based on configuration given to the shape memory element during forging.

Likewise, the embodiments of the present invention have been explained such that the fluid with a temperature higher than the temperature within the apparatus (e.g., hot fluid with temperature greater than normal body temperature) is used to facilitate the change in configuration of the shape memory element. However, in some other embodiments, fluid with a temperature lower than the temperature within the apparatus (i.e., cold fluid) may be used to facilitate the change in configuration of the shape memory element. As this cold fluid will heat to normal body temperature, the shape memory element may change its configuration from U-shape to the V-shape, and the apparatus will close.

Similarly, the present invention has been explained such that the shape memory element is disposed of adjacent to the elongate member and in certain embodiments, is embedded in one of the sidewalls of the elongate member that defines a lumen. Alternatively, in another embodiment, the shape memory element may be disposed within the lumen of the elongate member. In yet another embodiment, the shape memory element may have its own lumen such that it is disposed adjacent to an outer wall of the elongate member.

The present invention has been disclosed and described in terms of the treatment of fecal and urinary incontinence by controlling involuntary flow of fluids and substances in anus and urethra. The present invention may also find applications in controlling flow of fluids and substances through other body lumens. Moreover, the terms and expressions that have been disclosed in the specification are used as terms of description and not of limitation, and there is no intention of excluding equivalents of the features shown in the use of such terms and expressions.

In some embodiments, an apparatus for selectively opening and closing a body lumen within a patient's body includes an elongate member and a shape memory element. The elongate member is configured to at least partially surround the body lumen. The elongate member defines a lumen. The shape memory element is disposed adjacent to the lumen defined by the elongate member and adapted to change configuration based on a change in temperature of the shape memory element. The change in configuration of the shape memory element causing the apparatus to move between a first configuration and a second configuration.

In some embodiments, the first configuration is an open configuration and the second configuration is a closed configuration. In some embodiments, the elongate member is composed of a flexible material. In some embodiments, the elongate member is composed of a biocompatible material. In some embodiments, the lumen contains fluid. In some embodiments, the fluid is water. In some embodiments, the fluid is a biocompatible polymer.

In some embodiments, the apparatus includes a temperature control device for changing the temperature of the shape memory element. In some embodiments, the temperature control device is a heat exchanger. In some embodiments, the shape memory element is made of Nitinol. In some embodiments, the apparatus includes an insertion device for introducing fluid inside the lumen. In some embodiments, the apparatus includes a valve configured to facilitate introduction of the fluid inside the lumen. In some embodiments, the apparatus is used for the treatment of incontinence.

In some embodiments, an apparatus for selectively opening and closing a body lumen within a patient's body includes an elongate member configured to at least partially surround the body lumen, the elongate member defining a first lumen and a second lumen, wherein the first lumen is configured to receive fluid; and a shape memory element disposed within the second lumen, wherein the shape memory element is adapted to change configuration based on a change in temperature of the shape memory element, the change in configuration of the shape memory element causing the apparatus to move between a first configuration and a second configuration.

In some embodiments, the first configuration is an open configuration and the second configuration is a closed configuration. In some embodiments, the first lumen is at a first temperature. In some embodiments, the fluid is at a second temperature.

In some embodiments, the apparatus includes an insertion device for introducing the fluid inside the first lumen. In some embodiments, the apparatus includes a valve configured to facilitate introduction of the fluid inside the first lumen. In some embodiments, the apparatus includes a temperature control device for changing temperature of the fluid. In some embodiments, the apparatus is used for the treatment of incontinence.

In some embodiments, an apparatus for selectively opening and closing a body lumen within a patient's body includes and elongate member and a shape memory element. The elongate member is configured to at least partially surround the body lumen. The elongate member defines a first lumen and a second lumen, wherein the first lumen is configured to hold fluid. The shape memory element is disposed within the second lumen, wherein the shape memory element is adapted to change configuration based on a change in temperature of the shape memory element, the change in configuration of the shape memory element causing the apparatus to move between a first configuration and a second configuration.

In some embodiments, the first configuration is an open configuration and the second configuration is a closed configuration. In some embodiments, the fluid and the first lumen are at a first temperature. In some embodiments, the apparatus includes a temperature control device for changing temperature within the elongate member such that the fluid and the first lumen are at a second temperature.

In some embodiments, a method of selectively opening and closing a body lumen within a patient's body includes disposing of a device within the patient's body to at least partially surround the body lumen, wherein the device has a first temperature, the device comprising a shape memory element adapted to change configuration based on a temperature change; and introducing fluid inside the device, the fluid having a second temperature different than the first temperature, wherein the difference in temperature facilitates the change in the configuration of the shape memory element causing the device to move between a first configuration and a second configuration.

In some embodiments, the device is an elongate member. In some embodiments, the first configuration is an open configuration and the second configuration is a closed configuration.

In some embodiments, a method of selectively opening and closing a body lumen within a patient's body includes disposing of a device filled with fluid within the patient's body to at least partially surround the body, wherein the fluid is at a first temperature, the device comprising a shape memory element adapted to change configuration based on a temperature change; and changing the temperature of the fluid to a second temperature such that a change in temperature of the fluid causes a change in the configuration of the shape memory element causing the device to move between a first configuration and a second configuration.

In some embodiments, the device is an elongate member. In some embodiments, the first configuration is an open configuration and the second configuration is a closed configuration.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. An apparatus for selectively opening and closing a body lumen within a patient's body comprising:
    an elongate member configured to at least partially surround the body lumen, the elongate member including a sidewall, the sidewall defining a lumen;
    a shape memory element disposed within the lumen defined by the sidewall, the shape memory element adapted to change configuration based on a change in temperature of the shape memory element, the change in configuration of the shape memory element causing the elongate member to move between a first configuration and a second configuration thereby opening and closing the body lumen;
    a temperature control device for changing the temperature of the shape memory element, the temperature control device having a heating coil disposed within the lumen of the elongate member,
    wherein the lumen of the elongate member is configured to receive fluid, and heat generated via the heating coil is configured to be transferred to the fluid inside the lumen and subsequently to the shape member element.

2. The apparatus of claim 1, wherein the first configuration is an open configuration in which the elongate member has a substantially U-shape and the second configuration is a closed configuration in which a distance between ends of the U-shape is shorter than a distance between the ends of the U-shape of the first configuration.

3. The apparatus of claim 1, wherein the elongate member is composed of a flexible material.

4. The apparatus of claim 1, wherein the elongate member is composed of a biocompatible material.

5. The apparatus of claim 1, wherein the fluid is water.

6. The apparatus of claim 1, wherein the fluid is a biocompatible polymer.

7. The apparatus of claim 1, wherein the shape memory element is coupled to a surface inside the lumen of elongate member.

8. The apparatus of claim 1, wherein the temperature control device is a heat exchanger.

9. The apparatus of claim 1, wherein the shape memory element is made of Nitinol.

10. The apparatus of claim 1 further comprising an insertion device for introducing the fluid inside the lumen.

11. The apparatus of claim 10 including a valve configured to facilitate introduction of the fluid inside the lumen.

12. The apparatus of claim 1, wherein the shape memory element conforms to a shape of the sidewall of the elongate member, the shape of the sidewall of the elongate member including one or more curved portions.

13. An apparatus for selectively opening and closing a body lumen within a patient's body comprising:
   an elongate member configured to at least partially surround the body lumen, the elongate member including a sidewall, the sidewall defining a fluid lumen configured to receive fluid;
   a shape memory element disposed within the fluid lumen and at least partially embedded within the sidewall of the elongate member, wherein the shape memory element is adapted to change configuration based on a change in temperature of the shape memory element, the change in configuration of the shape memory element causing the elongate member to move between a first configuration and a second configuration thereby opening an closing the body lumen; and
   a temperature control device for changing the temperature of the shape memory element, the temperature control device having a heating coil disposed within the fluid lumen of the elongate member, the heating coil configured to heat the fluid,
   wherein heat generated via the heating coil is configured to be transferred to the fluid inside the fluid lumen and subsequently to the shape member element.

14. The apparatus of claim 13, wherein the first configuration is an open configuration and the second configuration is a closed configuration.

15. The apparatus of claim 13, wherein the shape memory element extends a length of the sidewall of the elongate member.

16. The apparatus of claim 13, wherein the fluid is at a second temperature.

17. An apparatus for selectively opening and closing a body lumen within a patient's body comprising:
   an elongate member configured to at least partially surround the body lumen, the elongate member defining a first lumen and a second lumen, wherein the first lumen is configured to hold fluid;
   a shape memory element disposed entirely within the second lumen such that the shape memory element is isolated from the fluid introduced into the first lumen, wherein the shape memory element is adapted to change configuration based on a change in temperature of the shape memory element, the change in configuration of the shape memory element causing the elongate member to move between a first curved configuration and a second curved configuration thereby opening and closing the body lumen;
   a first insertion device coupled to a first end of the elongate member, the first insertion device configured to transfer the fluid to or from the first lumen via a first opening at the first end;
   a second insertion device coupled to a second end of the elongate member, the second insertion device configured to transfer the fluid to or from the first lumen via a second opening at the second end; and
   a temperature control device for changing the temperature of the shape memory element, the temperature control device having a heating coil disposed within the first lumen of the elongate member,
   wherein heat generated via the heating coil is configured to be transferred to the fluid inside the first lumen and subsequently to the shape member element contained in the second lumen.

18. The apparatus of claim 17, wherein the first curved configuration is an open configuration and the second curved configuration is a closed configuration.

19. The apparatus of claim 17, wherein the fluid and the first lumen are at a first temperature.

* * * * *